(12) United States Patent
Fei

(10) Patent No.: US 10,172,529 B2
(45) Date of Patent: *Jan. 8, 2019

(54) SYSTEMS AND METHODS FOR DETECTING PHYSIOLOGICAL INFORMATION OF A USER

(71) Applicant: Physical Enterprises, Inc., Vancouver (CA)

(72) Inventor: Ming Shun Fei, Coquitlam (CA)

(73) Assignee: Beijing Shunyuan Kaihua Technology Limited, Haidian District, Beijing ( * ) Notice: Subject to any disclaimer, the term of this patent is extended or adjusted under 35 U.S.C. 154(b) by 503 days.

This patent is subject to a terminal disclaimer.

(21) Appl. No.: 14/472,157

(22) Filed: Aug. 28, 2014

(65) Prior Publication Data
US 2014/0371601 A1 Dec. 18, 2014

Related U.S. Application Data

(63) Continuation of application No. 14/468,916, filed on Aug. 26, 2014.
(Continued)

(51) Int. Cl.
*A61B 5/00* (2006.01)
*A61B 5/024* (2006.01)
*A61B 5/026* (2006.01)

(52) U.S. Cl.
CPC ........ *A61B 5/02427* (2013.01); *A61B 5/0261* (2013.01); *A61B 5/681* (2013.01);
(Continued)

(58) Field of Classification Search
CPC .............. A61B 5/02141; A61B 5/6824; A61B 5/02438; A61B 5/02427; A61B 5/6802; A61B 5/7203
See application file for complete search history.

(56) References Cited

U.S. PATENT DOCUMENTS

| 3,769,974 A | 11/1973 | Smart et al. |
| 4,880,304 A | 11/1989 | Jaeb et al. |

(Continued)

FOREIGN PATENT DOCUMENTS

| WO | WO2011051888 | 5/2011 |
| WO | WO2013106607 | 7/2013 |

*Primary Examiner* — Carolyn Pehlke
(74) *Attorney, Agent, or Firm* — Young Basile Hanlon & MacFarlane, P.C.

(57) ABSTRACT

Described herein are systems and methods for improving the reliability and accuracy of wearable physiological monitoring devices. A wearable monitoring device may comprise an inner surface configured for at least partial contact with a targeted tissue region of a person. The inner surface may comprise one or more outwardly projecting raised regions. The monitoring device may further comprise a physiological sensor, one or more components of which may be located at or near a raised region of the inner surface. In this manner, sufficient contact between the targeted tissue region and the inner surface, as well as proper placement of the one or more components of the sensor relative to the targeted tissue region, may be achieved. The accuracy and reliability of the monitoring device may also be less susceptible to the effects of ambient light and/or the movements of the user.

19 Claims, 8 Drawing Sheets

Related U.S. Application Data

(60) Provisional application No. 61/976,388, filed on Apr. 7, 2014.

(52) U.S. Cl.
CPC ............. *A61B 2560/0462* (2013.01); *A61B 2562/0233* (2013.01)

(56) References Cited

U.S. PATENT DOCUMENTS

| | | |
|---|---|---|
| 5,130,531 A | 7/1992 | Ito et al. |
| 5,237,994 A | 8/1993 | Goldberger |
| 7,067,893 B2 | 6/2006 | Mills et al. |
| 7,251,513 B2 * | 7/2007 | Kondoh ............... A61B 5/0059 600/310 |
| 9,226,663 B2 * | 1/2016 | Fei ....................... A61B 5/0059 |
| 2012/0197093 A1 | 8/2012 | LeBoeuf et al. |
| 2013/0060098 A1 | 3/2013 | Thomsen et al. |
| 2014/0127996 A1 * | 5/2014 | Park ..................... H04W 4/027 455/41.1 |
| 2014/0142403 A1 | 5/2014 | Brumback et al. |
| 2014/0206976 A1 | 7/2014 | Thompson et al. |
| 2014/0221854 A1 | 8/2014 | Wai |
| 2014/0288435 A1 | 9/2014 | Richards et al. |

\* cited by examiner

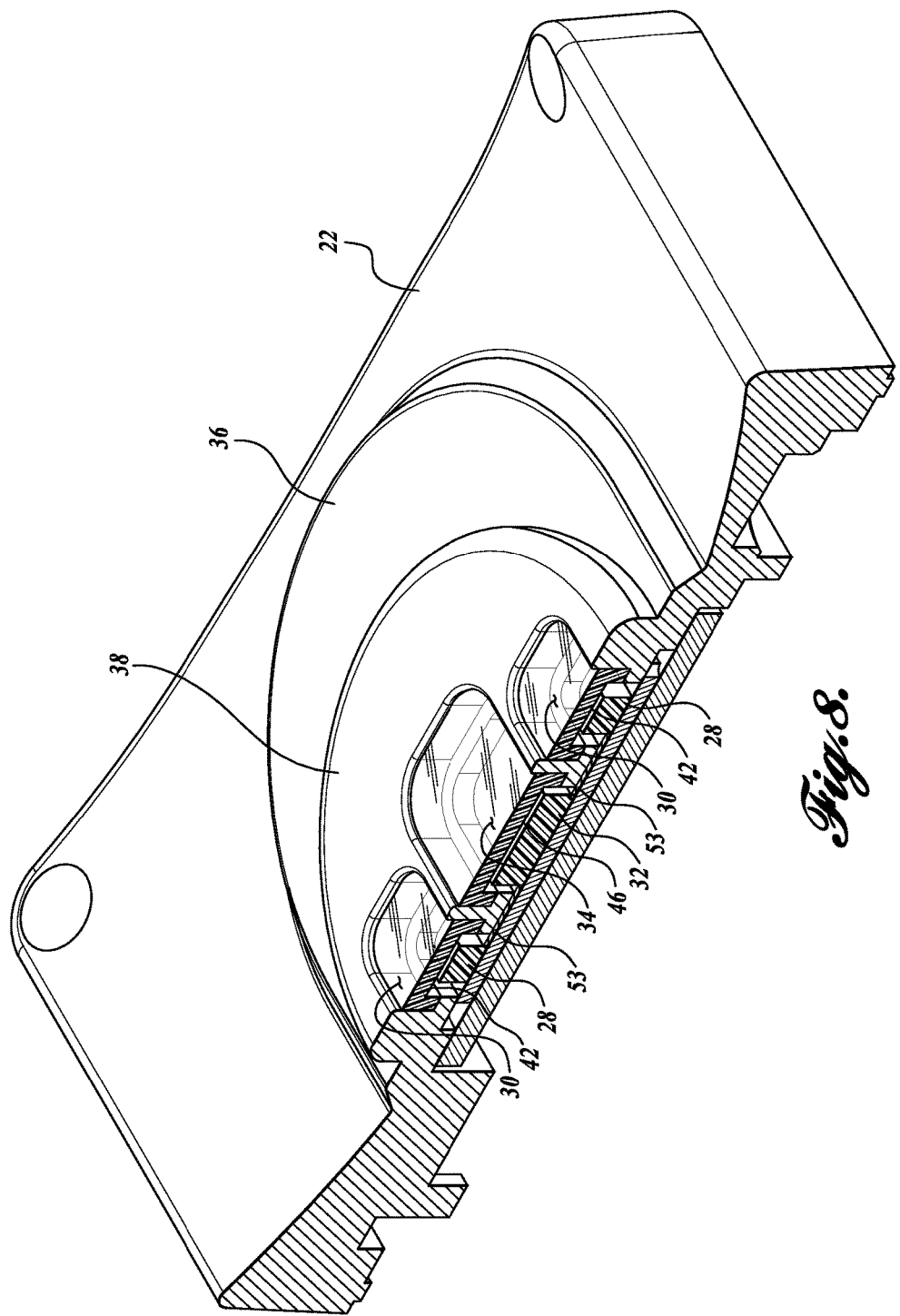

SYSTEMS AND METHODS FOR DETECTING PHYSIOLOGICAL INFORMATION OF A USER

This is a continuation application of U.S. patent application Ser. No. 14/468,916, filed Aug. 26, 2014, which claims the benefit of priority to U.S. Provisional Patent Application No. 61/976,388, filed Apr. 7, 2014, both of which are expressly incorporated herein by reference.

FIELD OF THE DISCLOSURE

The embodiments relate generally to systems and methods for the sensing or measuring of physiological information associated with a user. More particularly, the embodiments relate to a wearable device comprising a physiological monitoring sensor.

BACKGROUND

Numerous portable devices have been developed in which optical sensors are used to detect, measure, and display various physiological parameter information of a user. For example, some devices detect and measure the variation in blood flow through arteries or blood volume in subcutaneous tissue. Applications for such optical sensors include the monitoring of heart rate, glucose level, apnea, respiratory stress, and other physiological conditions. The optical sensor of such arrangements include one or more light sources that illuminate a targeted portion of the human body and one or more associated optical detectors that receive a portion of the optical energy emitted by the light sources. There are two basic types of such arrangements. In transmissive sensor arrangements, a relatively thin portion of the body such as the tip of the finger or the earlobe is positioned between a light source and a photo detector. Light that passes through the body tissue impinges on the photo detector resulting in an electrical signal that is synchronized to each heartbeat. In reflective sensor arrangements, a sensor that includes one or more light sources located in spaced apart juxtaposition with a photo detector is positioned against a targeted area of the body. Optical energy emitted by the light sources passes through the skin of the targeted tissue region, is scattered, partially absorbed, and is reflected by the body (e.g., blood flowing through arteries and other vascular structure). In some applications, the reflected optical energy is in effect modulated in accordance with blood flow in the targeted area and detected by the photo detector. The detected reflection can then be used to produce a signal pulse that is synchronized to each heartbeat. In both transmissive and reflective arrangements, the signal produced by the photo detectors is processed to display or otherwise provide a real time indication of the monitored physiological parameter.

One area of growing interest in the use of physiological monitors is with respect to personal wellness and/or physical exercise for purposes of fitness training and weight loss. Technological advances relating to optical sensors, signal processing, and display devices have made it possible to realize small, light-weight physiological monitors that can be embodied as armbands or bracelets that are comfortably worn by a user. For example, the embodiments described herein comprises an optical sensor that may be included in a wearable device.

Providing physiological monitors for wellness and physical exercise applications is subject to numerous design and manufacturing considerations. For example, the electronic circuitry for processing the signal produced by the photo detector and displaying an indication of the monitored parameter must operate at a low power level to provide adequate battery life while simultaneously providing sufficient accuracy. Constraints relating to the physical design of such monitors are not limited to the challenges of packaging the electronics and display units in an arrangement that can be easily and comfortably worn by a user. Special considerations and constraints are present with respect to incorporation of the optical sensor. For example, the light sources and photodiode of the optical sensor must be optically isolated from one another. Otherwise, the photo detector will receive optical energy that is not modulated by heartbeat, which can result in an unwarranted increase in electrical design requirements and/or seriously affect monitoring accuracy and power requirements. Similarly, optimal performance requires that the optical sensor be firmly positioned against the user's skin so that light emitted by an optical source passes through the skin and, additionally, so that ambient light does not reach an associated photo detector. Firmly positioning the optical sensor against the user's skin also is important with respect to preventing movement of the sensor that can affect the accuracy of the monitoring device and/or interrupt its operation. Additionally, the optical sensor should be securely retained by the monitoring device to maintain physical integrity and facilitate satisfactory waterproofing of the entire monitor.

Because of the above mentioned design and manufacturing considerations, as well as others that are known to designers and manufacturers, a need exists for improved systems and techniques for incorporating optical sensor arrangements in physiological monitoring devices. The need is of special significance relative to personal wellness, activity, sleep, and exercise monitors. In particular, the manufacturing costs of such devices must be maintained as low as possible to provide a generally affordable and competitive product without sacrificing product accuracy and quality.

SUMMARY OF THE DISCLOSURE

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure describes systems and methods for sensing, measuring, displaying, or otherwise communicating physiological parameter information of a user. In one aspect, the physiological monitoring devices disclosed herein may be wearable devices that can be secured to the body of the user. The monitoring devices may be used in the context of, for example, physical training, activity tracking, wellness monitoring, sleep monitoring, and/or other suitable activities.

In one aspect, an apparatus disclosed herein may comprise a housing comprising a front face, a rear face, and an interior region located between the front face and the rear face. At least a portion of the rear face may be configured for contact with a targeted tissue region of a person. The rear face may also comprise one or more raised regions projecting outward toward the targeted tissue region. The apparatus may further comprise a sensor for sensing physiological information or events. The sensor, or at least a portion thereof, may be located within the one or more raised regions. In this manner, adequate contact between the rear face of the housing and the targeted tissue region, as well as proper placement of one or more components of the sensor with respect to the targeted tissue region, may be achieved.

In another aspect, a device disclosed herein may comprise an elongate body having a front face, a rear face, and an interior region located between the front and rear faces. At least a portion of the rear face may be configured for contact with a targeted area of a user. The rear face may further comprise an outwardly protruding region having at least one aperture configured for at least partially receiving a respective component of a sensor for sensing physiological information.

In a further aspect, a wearable apparatus disclosed herein may comprise a body having a rear face configured for at least partial contact with a targeted area. The wearable apparatus may further comprise a sensor comprising at least one light source, at least one optical detector, and at least one transparent, substantially transparent, or translucent member. The rear face of the body may comprise a base region and a raised region extending beyond the base region. One or more components of the sensor may be at least partially positioned within the raised region proximate or in contact with the targeted area.

Additional objects and advantages of the present disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are illustrative and explanatory only and are not restrictive of the claims.

The accompanying drawings, which are incorporated in and constitute a part of this specification, illustrate several embodiments and together with the description, serve to explain the principles of the disclosure.

BRIEF DESCRIPTION OF THE DRAWINGS

FIG. 8 depicts some aspects of an illustrative embodiment of an apparatus as described herein.

DESCRIPTION OF THE EMBODIMENTS

Figure 1:
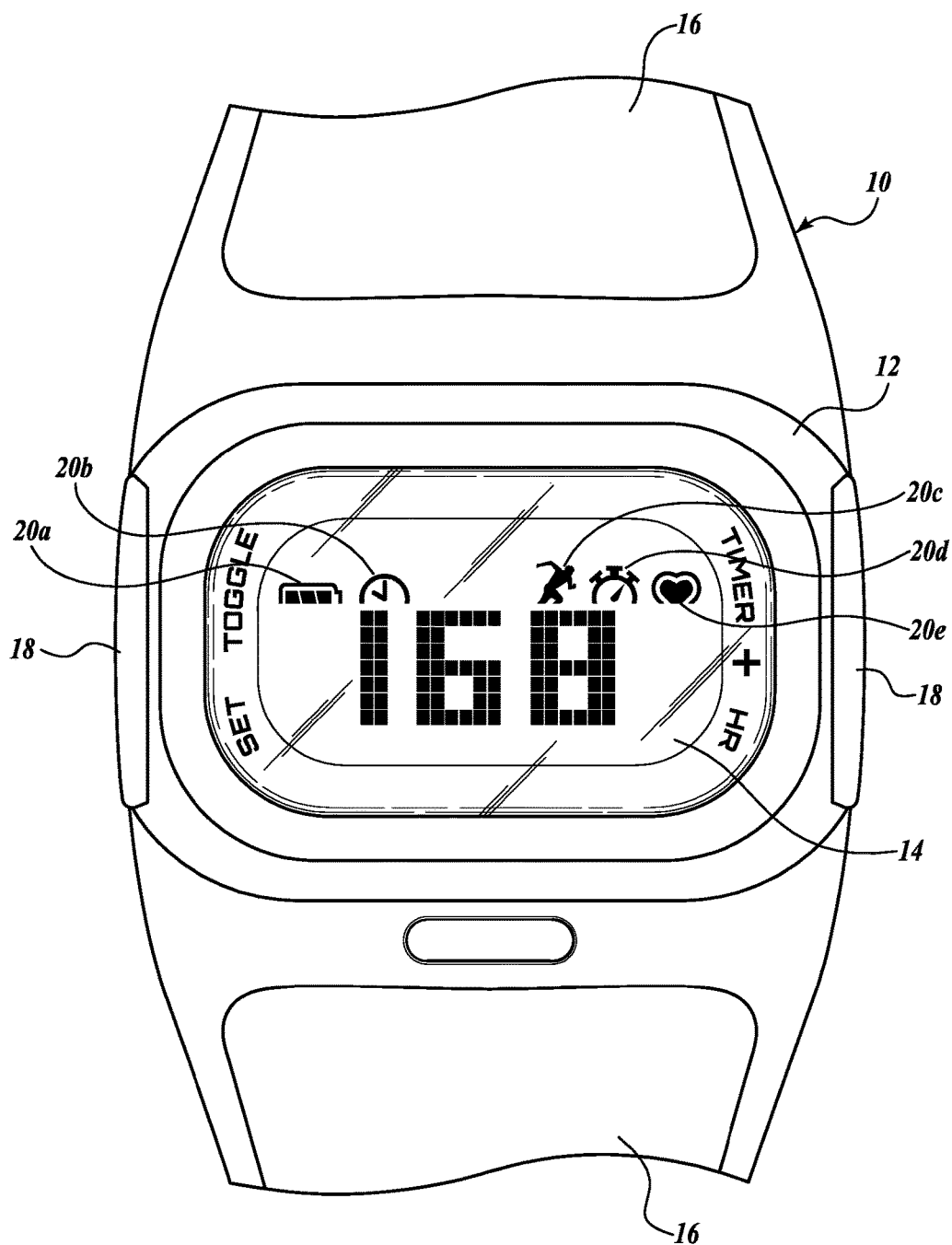
FIG. 1 depicts some aspects of an illustrative embodiment of an apparatus as described herein.

Shown in FIG. 1 is an apparatus 10 comprising an optical sensor and components for processing and displaying a physiological parameter of a user, as well as other information that may or may not be directly related to the user's activity or environment. In one embodiment, the physiological parameter may be heart rate information. In other embodiments, however, other physiological information may be displayed. As depicted in FIG. 1, apparatus 10 may be a watch, however, apparatus 10 may also be a band, strap, or any other wearable device configured for securing to a user's body or an appendage thereof.

In one embodiment, apparatus 10 may house a display unit 14 for displaying or otherwise conveying information to the user. In one embodiment, the display unit 14 may comprise a dot matrix liquid crystal display 14. In alternative embodiments, the display unit 14 may comprise some other suitable display or one or more light sources for conveying information. In still further embodiments, apparatus 10 may comprise no display unit. Rather, information collected, measured, or stored at apparatus 10 may be communicated to the user by some other means, such as wired or wireless transmission to another device or external display.

In another aspect, apparatus 10 may comprise a housing 12 and a pair of bands 16 extending from opposite edges of the housing 12 for securing apparatus 10 to the user. In other embodiments, apparatus 10 may comprise a single band 16 and have no housing. In such embodiments, one or more components of apparatus 10 may be embedded or located within band 16.

In one embodiment, bands 16 may comprise a flexible or rigid elastomeric, plastic, silicone, or polymer material. In alternative embodiments, bands 16 may comprise some other suitable material, including but not limited to, a fabric, woven, or metal material.

Apparatus 10 may further comprise one or more switches 18 operable for accepting input from the user. In one embodiment, switches 18 may extend along the narrow edges of housing 12. In other embodiments, switches 18 may be located elsewhere on housing 12 or along band 16.

In use, the user may manipulate switches 18 for, among other things, establishing an operational mode of apparatus 10, inputting user-specific information such as sex, height, weight, etc., entering a date or time, navigating one or more menus, or inputting other information. In one aspect, switches 18 may comprise any switch, button, or sensor configured to accept input from the user. In alternative embodiments, switches 18 may be incorporated into display unit 14. For example, switches 18 may comprise "soft" buttons configured to accept input from the user via a touchscreen. FIG. 1 depicts a pair of switches 18, one positioned on either side of the housing 12. Other embodiments, however, may comprise fewer or additional switches.

Housing 12 or straps 16 may further comprise switch indicators for providing the user with information regarding each switch. In one embodiment, housing 12 or straps 16 may comprise words and/or symbols such as "set," "toggle," "timer," "+," and "HR" corresponding to the switches and providing the user with an indication of a function to be achieved by manipulation of the respective switch. Of course, the switch indicators depicted in FIG. 1 are only illustrative of the possibilities. Housing 12 or bands 16 may comprise fewer, additional, or alternative indicators.

In an embodiments comprising display unit 14, the display may comprise one or more small icons for conveying information to the user. In one embodiment, the one or more icons may be located in an upper portion of the display 14 to indicate operational and/or conditional aspects of apparatus 10. In the depicted embodiment, icon 20a may be illuminated whenever the watch is energized to indicate battery condition; icon 20b may be illuminated when display 14 indicates the time of day; icon 20c and 20e may be illuminated when apparatus 10 is monitoring, measuring, or displaying physiological parameter information (e.g., heart rate information); and icon 20d may be illuminated when apparatus 10 is operating in an activity mode and/or an activity duration is being recorded. As also is indicated in FIG. 1, physiological parameter information (e.g., the user's heart rate or some other detected or measured parameter) may be displayed in a central region 20f of display 14. The same display region may also display a date, time, or other information when apparatus 10 is in different operational states. Of course, the aforementioned examples of icons 20a-20f and/or each icon's respective size and position within display unit 14 are only illustrative of the possibilities. Fewer, additional, or alternative icons and/or icon size and placement is also possible.

Alternatively or additionally, apparatus 10 may comprise a communication status indicator 21. In one embodiment, the status indicator 21 may comprise an outward facing light source viewable by the user when the watch is in use. In some embodiments, the light source may comprise one or more lights, such as LEDs. In further embodiments, the light source may comprise a plurality of LEDs, each of a different color. In this manner, the color of the LED illuminated may convey additional information to a user regarding the communication status of apparatus 10. For example, when apparatus 10 may be in communication with another device via a suitable communication channel, such as Bluetooth communication, status indicator may illuminate light of a first color. Where apparatus 10 may be in communication with another device via some alternative communication channel, status indicator 21 may illuminate light of a second color. Alternatively, or additionally, status indicator 21 may illuminate light of another color when ongoing communication with another device may be terminated and/or apparatus 10 ends or initiates an operational state. Again, these examples are only illustrative of the possibilities and status indicator 21 may illuminate one or more light sources corresponding to one or more colors to indicate or convey any suitable information to the user. Moreover, in an embodiments of apparatus 10 that do not comprise a display unit 14, status indicator may convey some or all of the information described above with respect to display unit 14.

Figure 2:
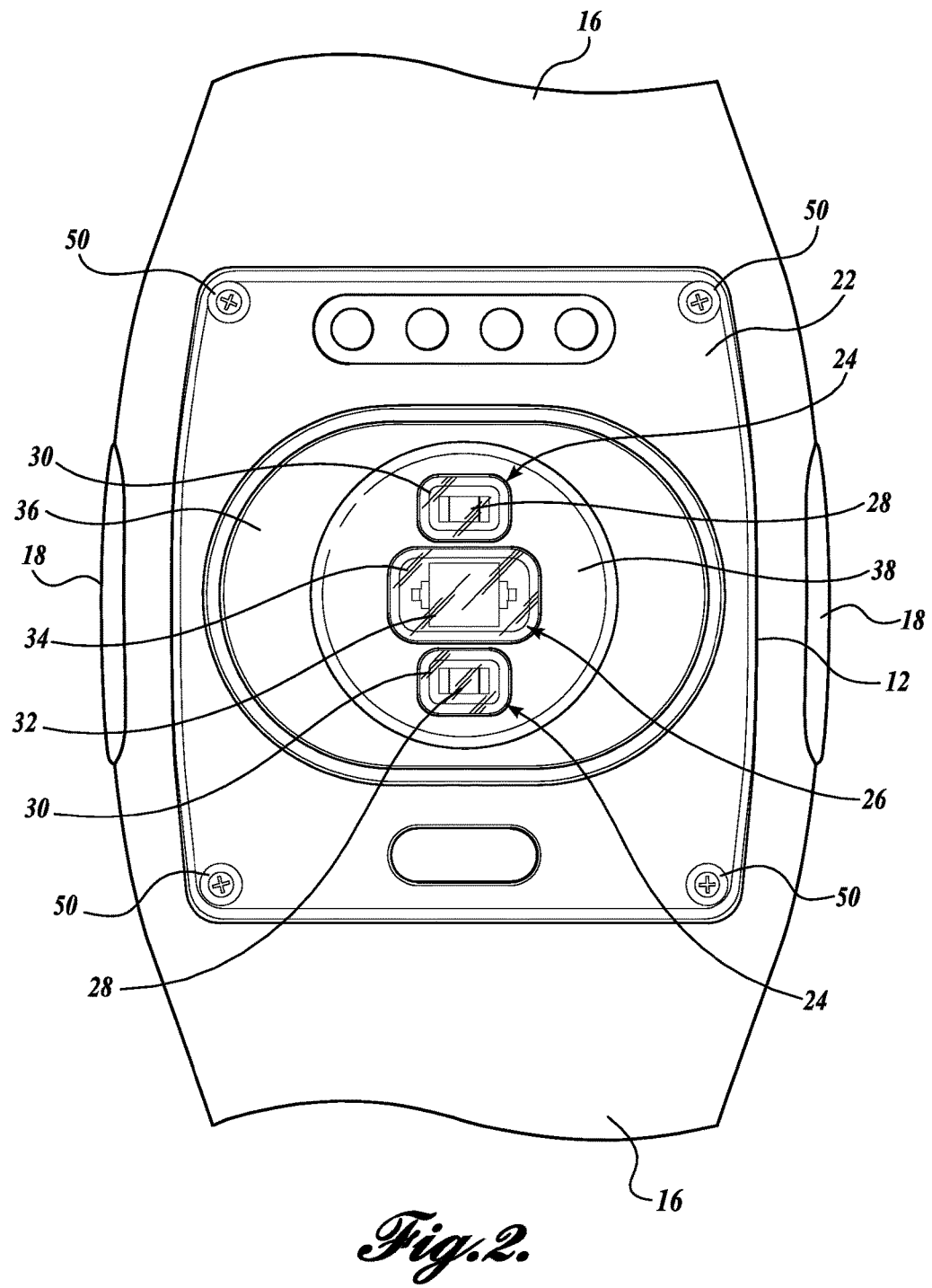
FIG. 2 depicts some aspects of an illustrative embodiment of an apparatus as described herein.

FIG. 2 depicts an embodiment of the back of apparatus 10 comprising a caseback 22. Caseback 22 may be secured to apparatus 10 using any suitable attachment system or method. For example, as depicted in FIG. 2, caseback 22 may be secured to apparatus 10 by one or more screws 50 or some other suitable attachment mechanism. Alternative embodiments may comprise a caseback integrated with straps 16 such that no attachment mechanism is needed. Other embodiments may comprise no caseback at all. Rather, strap 16 may comprise one or more integral or discrete components or structure substantially similar or corresponding to those described below with respect to caseback 22, i.e., where a caseback, structure of a caseback, or a component positioned within a caseback may be described herein, corresponding structure and/or locating of components may be achieved in straps 16 and a caseback may not be necessary.

In one embodiment, caseback 22 may comprise an optical sensor as described herein. Specifically, the optical sensor may comprise one or more light sources. As depicted in FIG. 2, the optical sensor may comprise two light sources 24 that may be spaced apart from one another. Alternative embodiments may comprise fewer or additional light sources. In the depicted arrangement, each light source 24 may include one or more LEDs 28 that may be contained in a respective lens 30. In that regard, it should be noted that lens 30 may not necessarily be the same as, nor replace, the integral lens of a conventional LED, which is configured to cause emitted light to pass from an end surface of the device.

In another aspect, one or more optical detectors 26 may be located between, adjacent, or proximate light sources 24. In one embodiment, the one or more optical detectors may comprise one or more photodiodes 32 that may be contained by a corresponding lens 34.

As depicted in FIG. 2, one or more optical detectors 26 may be positioned between, equidistant, and symmetrically aligned with respect to a pair of light sources 24. Such an embodiment, however, is only illustrative of the possibilities and other suitable configurations are also possible. For example, in other embodiments, optical detector 26 may be fully or partially encircled by one or more light sources 24. Alternatively, optical detector 26 may not be symmetrically situated between the one or more light sources, i.e., optical detector 26 may be positioned closer to one or more light sources than one or more other light sources. In still further embodiments, optical detector 26 may not be located between the two or more light sources. The location and number of optical detectors 26 and light sources 24 may also be reversed from that shown in FIG. 2. For example, the optical sensor may comprise a light source 24 located between, adjacent, or proximate one or more optical detectors 26.

In some embodiments, lenses 30 and 34 may comprise a mineral glass or a plastic that may exhibit a high degree of optical transmission at wavelengths of the optical energy emitted by LEDs 28. In alternative embodiments, lenses 30 and 34 may comprise some other suitable material. In some instances it may be possible to form lens 30 and 34 from material that imparts a filtering effect to the lenses. For example, ambient light that reaches photodiode 32 may be noise that can affect the operation and/or accuracy of apparatus 10. In embodiments in which LEDs 28 emit light sufficiently removed from the infrared region, it may be advantageous to use lenses that block a portion of incident infrared energy to thereby decrease the effect of any ambient light that may pass between caseback 22/strap 16 and the user's tissue. In still further embodiments, one or more of lenses 234 and 244 may comprise an epoxy layer or encasement poured or placed into caseback 220 rather than a glass or plastic lens. Such an epoxy layer may be pre-formed or formed with a respective light source or optical detector positioned within caseback 220. In such embodiments, the epoxy layer may be separated from the respective LED 232 or photodiode 242 by a barrier or by space. Alternatively, the epoxy may completely or partially encase the respective LED 232 or photodiode 242.

In another aspect, caseback 22 may be configured such that the optical sensor may be in contact or urged firmly against the skin when apparatus 10 is worn by a user. In that regard, caseback 22 may comprise a raised region 36 that may project outwardly from the surface of caseback 22.

In some embodiments, centrally located in raised region 36 may be a further raised region 38. The raised and further raised region may serve to adequately urge the optical sensor against the user's skin. As mentioned above, in embodiments that do not comprise a caseback 22, raised region 36 and/or further raised region 38 may be formed in, or attached to, strap(s) 16.

In one aspect, the surface of LED lenses 28 and optical detector lens 34 may be substantially flush with or extend slightly above the surface of the further raised region 38. Of course, in other embodiments, caseback 22 may comprise only one of raised region 36 and further raised region 38. Alternatively, caseback 22 may comprise additional raised regions. Moreover, while FIG. 2 depicts raised region 36 as a substantially elliptical region and further raised region 38 as a substantially circular raise region, other suitable shapes of the raised region and further raised region are possible and the depicted embodiments should not be construed to limit the possibilities.

Figure 3:
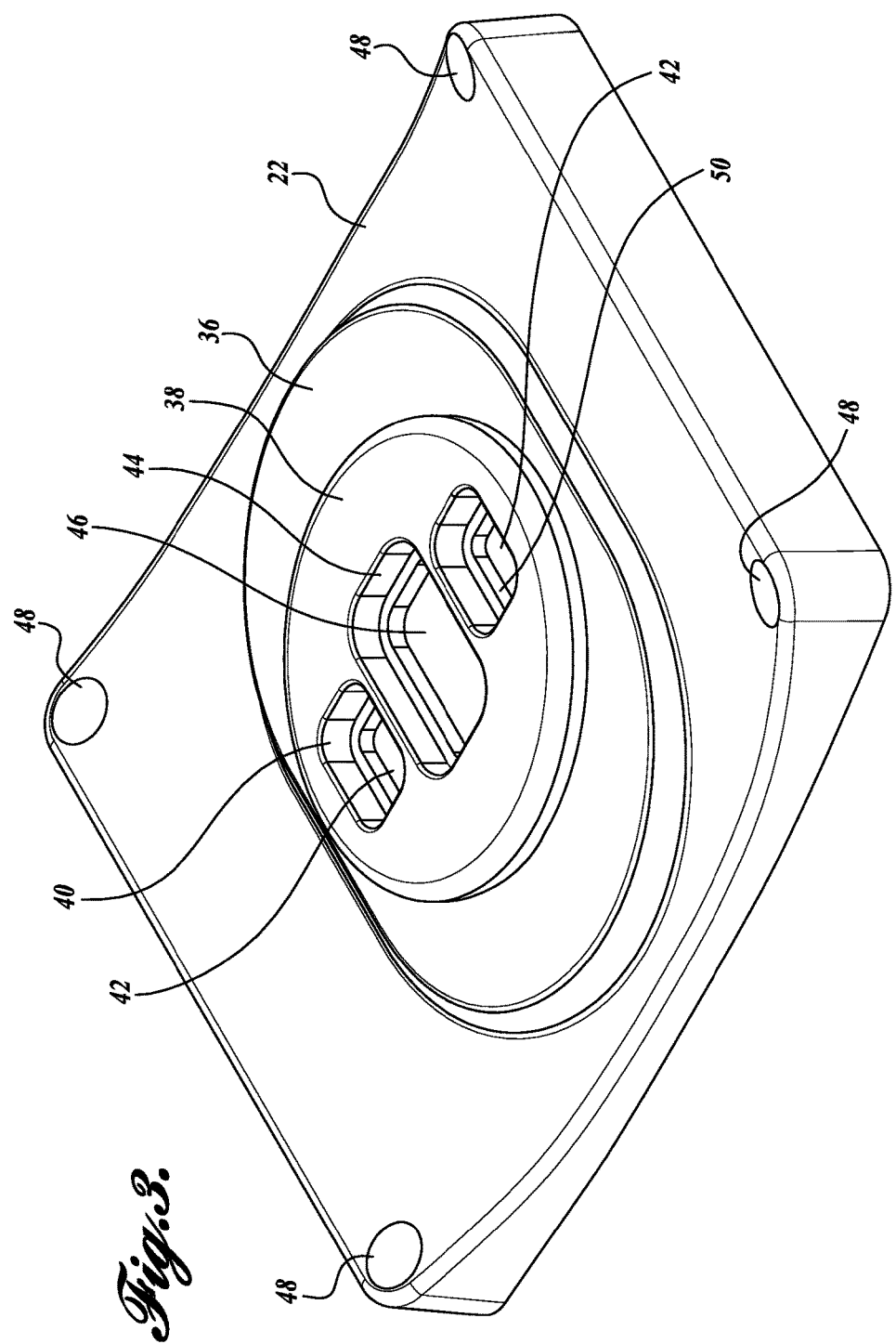
FIG. 3 depicts some aspects of an illustrative embodiment of an apparatus as described herein.
Figure 4:
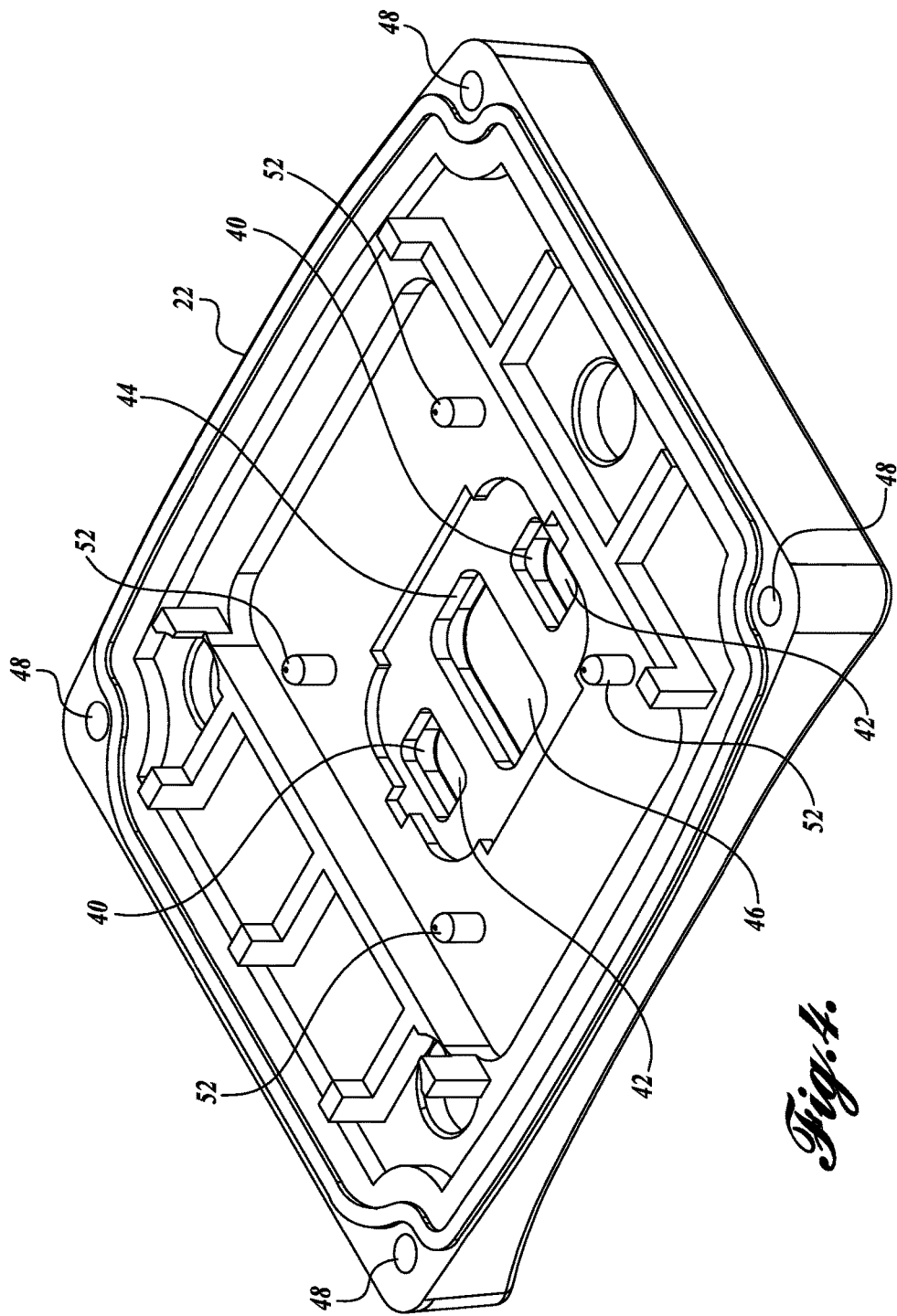
FIG. 4 depicts some aspects of an illustrative embodiment of an apparatus as described herein.

FIGS. 3 and 4 respectively, illustrate the back and interior of caseback 22 prior to the installation of LEDs 28, LED lenses 30, photodiode 32 and optical detector lens 34. Again, in embodiments that do not comprise a caseback 22, some or all of the structure depicted in FIGS. 3 and 4 may be formed in, or attached to, strap(s) 16. For example, in one embodiment, strap(s) 16 may comprise a pair of adjacent layers, one or both of which may comprise some or all of the structure depicted in FIGS. 3 and 4. The layers may then be attached, joined, or adhered to one another in any suitable manner to create a structure substantially similar to that described herein with respect to caseback 22 and the remainder of apparatus 10.

As can be seen in both FIGS. 3 and 4, recesses 40 may extend inwardly into the back of caseback 22 for receiving LED lenses 30. The interior of each recess 40 may be shaped to substantially correspond with the exterior configuration of a lens 30. An opening 42 may be located at the bottom of each recess 40 for receiving an LED 28. Each opening 42 may be smaller than the cross-sectional area of the associated recess 40 so that an inwardly-extending ledge may be formed around the lower periphery of the recess 40. When an LED lens 30 is inserted in the recess 40, the bottom of the lens may come into abutment with the ledge and the face of the lens may be flush with, or project slightly beyond, the rear face of caseback 22.

Similarly, a recess 44 may extend inwardly in caseback 22 for receiving optical detector lens 34. The configuration of recess 44 may correspond to that of recesses 40 in that the interior wall of recess 44 may be configured to substantially correspond with the exterior configuration of optical detector lens 34. An opening 46 may be located at the bottom of recess 44 for receiving optical detector lens 43. Opening 46 may be smaller than the cross-sectional area of recess 44 so that an inwardly extending ledge may be formed around the lower periphery of recess 44. When an optical detector lens 34 is inserted in the recess 44, the bottom of the lens may come into abutment with the ledge and the face of the lens may be flush with, or project slightly beyond, the rear face of caseback 22.

In view of FIGS. 3 and 4, it may be recognized that recesses 40 and 44 may establish the position of LED lenses 30 relative to optical detector lens 34. This, in turn, may establish the distance and positional relationship between LEDs 28 and photodiode(s) 32. In practice, recesses 40 and 44 may be positioned to ensure that sufficient light emitted by LEDs 28 may reach photodiode 32 after being reflected by the user's body (e.g., blood flowing through arteries and other vascular structure). As described previously, the particular location of recesses 40 and 44, as shown in FIGS. 3 and 4 is only illustrative and other suitable locations may be possible.

As also can be seen in FIG. 3, the rear face of caseback (or strap(s) 16, in embodiments with no caseback) may be contoured to substantially correspond with the wrist or forearm of the user. In one embodiment, openings 48 may be located in each corner of caseback 22 for threaded fasteners 50 (depicted in FIG. 2) that may secure caseback 22 to case 12 of FIG. 1. Additionally, as shown in FIG. 4, four placement posts 52 may extend from caseback 22 to ensure proper placement of a circuit board comprising one or more of LEDs 28 and photodiode(s) 32. Proper placement of the circuit board may, in turn, ensure proper positioning of the LEDs and/or photodiode(s) with respect to caseback 22 and/or corresponding LED lenses 30 and/or optical detector lens 34. In one embodiment, placement posts 52 may be cylindrical in shape and may be located so as to form a rectangular pattern extending toward the interior of caseback 22. In alternative embodiments, placement posts 52 may exhibit some other suitable shape and/or may be positioned in another arrangement for ensuring proper positioning of the circuit board, LEDs 28, and/or photodiode 32.

Figure 5:
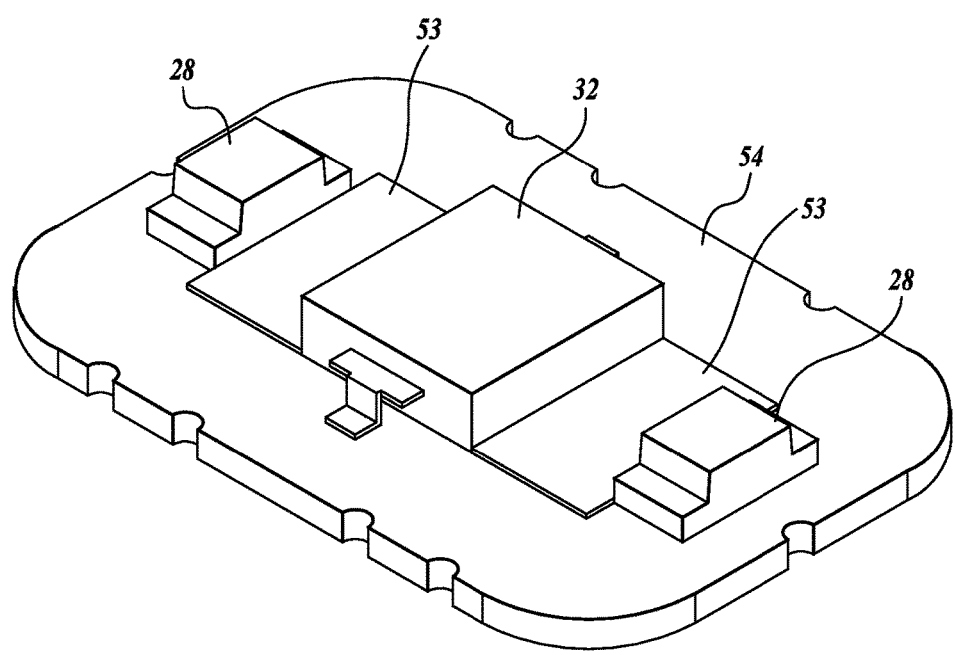
FIG. 5 depicts some aspects of an illustrative embodiment of an apparatus as described herein.

FIG. 5 depicts an arrangement for mounting LEDs 28 and photodiode 32. In the depicted arrangement, LEDs 28 and photodiode 32 may be positioned relative to one another by means of a printed circuit board 54 that electrically connects the devices to other circuitry contained in apparatus 10 (not shown). In one embodiment, a relatively thin strip of opaque pliant material 53 (such as, but not limited to, a tape, a sponge-like polymer, or an epoxy) may extend between the edges of photodiode 32 and the adjacent edges of LEDs 28. As described relative to the assembled caseback (FIGS. 7 and 8) opaque strips 53 may prevent light emitted by the LEDs from travelling along the surface of printed circuit board 54 and reaching photodiode(s) 32.

Although FIG. 5 depicts LEDs 28 and photodiode 32 on a single circuit board, alternative embodiments comprising a plurality of circuit boards in communication with one another are also possible. In such embodiments, commands to and/or measurements from LEDs 28 and photodiode(s) 32 may be communicated via one or more wired or wireless communication channels.

Figure 6:
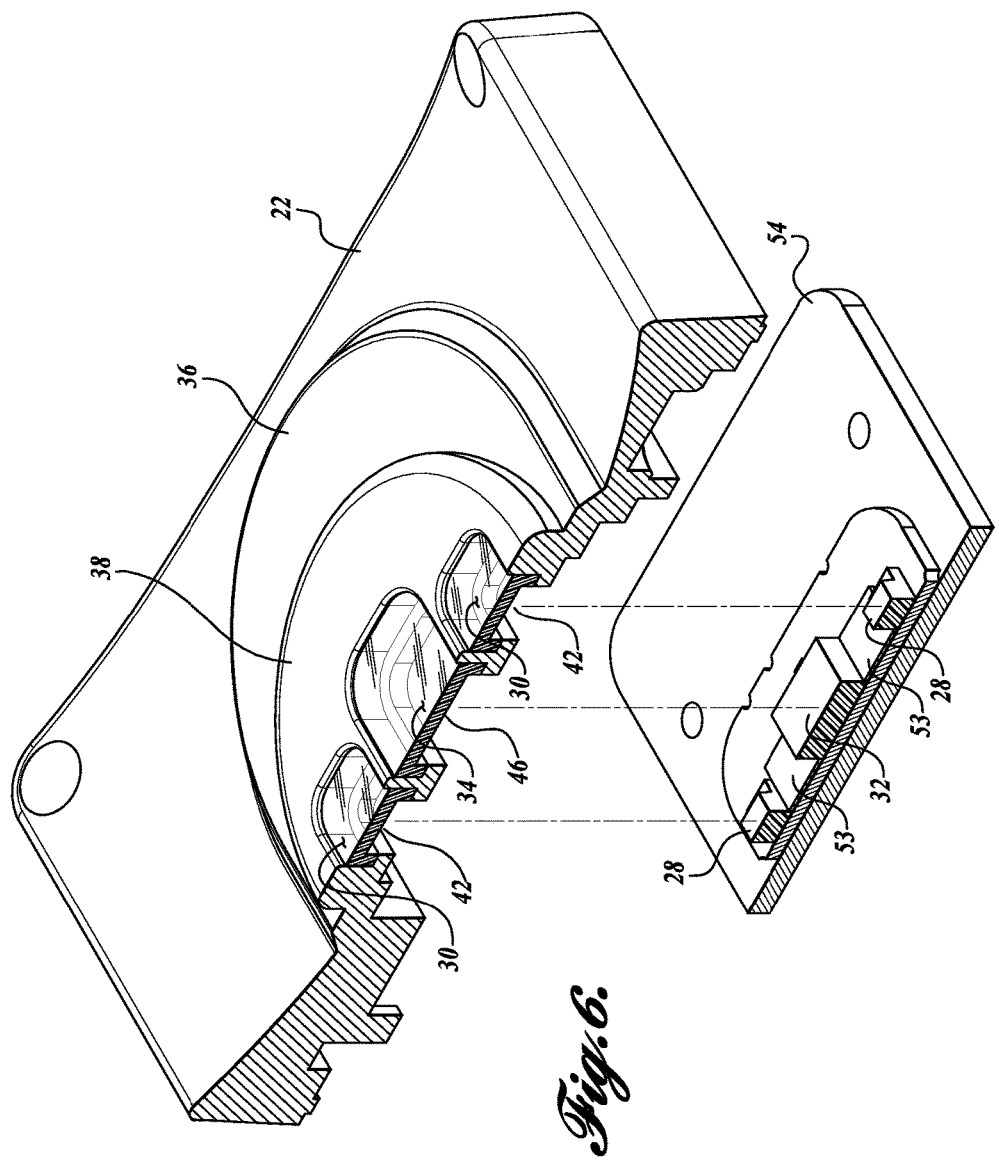
FIG. 6 depicts some aspects of an illustrative embodiment of an apparatus as described herein.

FIG. 6 is a partially cutaway view of caseback 22 and printed circuit board 54 that illustrates one possible manner in which the optical sensor may be incorporated in caseback 22 (or strap(s) 16 in embodiments that do not comprise a caseback). In FIG. 6, LED lenses 30 may be inserted and sealed in recesses 42 of FIGS. 3 and 4. As previously indicated, the light-emitting surface of each lens 30 may be substantially flush with, or extend slightly above, the surface of further raised region 38.

In a like manner, optical detector lens 34 may be inserted and sealed in recess 44 of FIGS. 3 and 4. The light-receiving surface of lens 34 may be substantially flush with, or extend slightly above, the surface of further raised region 38. Various techniques can be used for bonding LED lenses 30 and optical detector lens 34 to caseback 22. For example, depending in part of the material being used for caseback 22 or strap(s) 16, the lenses may be bonded in place by a curable adhesive, ultrasonic bonding or other techniques. In some applications, insert molding or cold-molding techniques may be employed. As indicated by phantom lines in FIG. 6, LEDs 28 and photodiode(s) 32 may pass into openings 42 and 44 so that LEDs 28 may be at least partially contained or received by lenses 42 and photodiode(s) 32 may be at least partially contained or received by optical detector lens 34.

Lenses such as those depicted in FIGS. 2 and 6-8 may be advantageous with respect to product manufacture, eliminating the prior use of a transparent epoxy resin to encapsulate the sensor elements in openings formed in the rear face of the watch. Not only may device assembly be simplified, but the process of device and/or component repair may be made more efficient. Moreover, light transmission through one or more lenses may be superior (i.e., less loss, noise, scatter, etc.) to light transmission through an epoxy. This, in turn, may enhance overall device performance, including the emitting and detecting of light to and from a targeted area. In some embodiments, the protrusion height of one or more raised region 36 and further raised region 38 may be less pronounced or protrude a shorter distance from the device where glass or plastic lenses are used.

Figure 7:
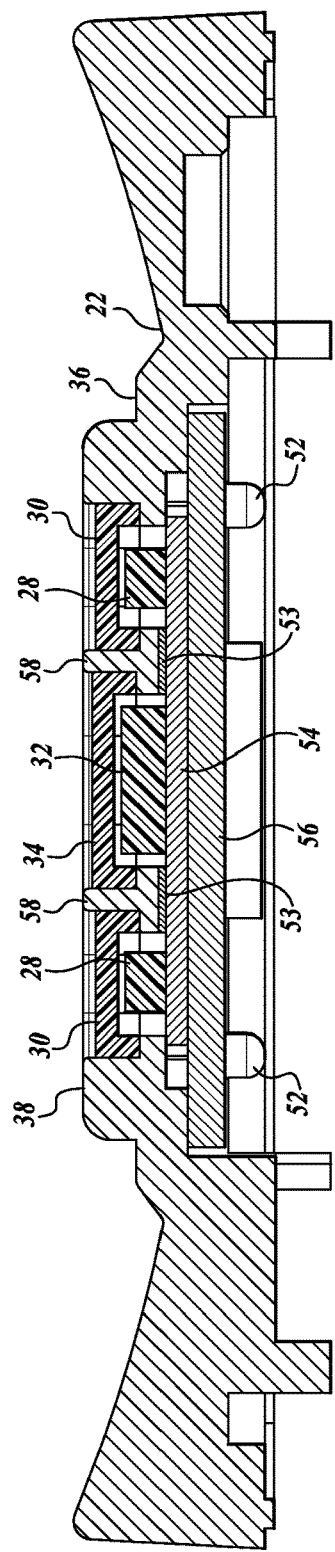
FIG. 7 depicts some aspects of an illustrative embodiment of an apparatus as described herein.

FIG. 7 depicts a cross-sectional view of one embodiment of apparatus 10 comprising caseback 22, LEDs 28, photodiode 32 and the associated lenses 30 and 34. As can be seen in FIG. 7, printed circuit board 54 (described relative to FIGS. 5 and 6) may be positioned on the upper surface of a circuit board 56. In one embodiment, circuit board 56 may include circuitry for detecting and displaying one or more physiological parameters of a user (e.g., a user's heart rate), the time of day and other information (not shown). Mounting posts 52, extending from caseback 22 and through or about circuit boards 54 and 56 (FIG. 4) may maintain circuit boards 54 and 56 in a fixed position within caseback 22. LEDs 28 may extend into corresponding lenses 30 and photodiode 32 may extend into corresponding photo detector lens 34. In other embodiments, circuit board 56 may not be positioned below printed circuit board 54. Rather, circuit board 56 may be located at another position along the longitudinal extension of strap(s) 16. In such embodiments, printed circuit board 54 and circuit board 56 may be in communication with one another through a suitable wired or wireless communication channel. In alternative embodiments, apparatus 10 may not comprise a second circuit board.

FIG. 7, alone and in combination with FIG. 8, may illustrate optical isolation of photodiode 32 from LEDs 28. As described relative to FIG. 3, the openings 42 for receiving LEDs 28 may be smaller than the recesses 40 for receiving LED lenses 30. Likewise, the opening 46 for receiving photodiode 32 may be smaller than the recess 44 for receiving the optical detector lens 34. In this manner, each combination of LED 28 and LED lens 30 may be physically and optically separated from the combination of photodiode 32 and optical detector lens 34 by a respective barrier 58 that may extend downwardly from further raised region 38 of caseback 22 to the base of the LEDs 28 and photodiode 32. In one embodiment, each barrier 58 may comprise an inverted T-shaped barrier. As is shown in FIG. 7, the inner edges of LED lenses 30 may be separated from the outer edges of optical detector lens 34 by an upwardly extending leg of the T-shaped barrier 58 and the inner edges of LEDs 28 may be separated from the outer edges of photodiode 32 by a laterally extending lower leg of the T-shaped barrier 58. In addition, the bottom surface of laterally extending lower leg of each T-shaped barrier 58 may contact and/or press against the opaque strips 53 (shown and described relative to FIG. 5) to further ensure that light emitted by LEDs 28 does not reach photodiode 32 without being reflected by a targeted region of the user.

While illustrative embodiments have been illustrated and described, it will be appreciated that various changes can be made therein without departing from the spirit and scope of the disclosure. For example, those skilled in the art will recognize that the disclosure can be practiced with a variety of physiological monitoring devices and that various light emitting and photo detecting devices may be employed. In some situations it may be appropriate to use one or more lenses that are configured for receiving more than one optical sensor in a single lens and/or to use one or more lenses that are configured for receiving more than one light source in a single lens. Furthermore, while some figures described herein may depict a watch-like embodiment, other embodiments may comprise fewer, additional, or alternative features similar to common fitness bands and/or other wearable devices for monitoring physiological information, including bands comprising a single strap or devices that may or may not comprise a display unit for displaying alphanumeric information.

It is intended that this specification and the aforementioned examples and embodiments be considered as illustrative only, with the true scope and spirit of the disclosure being indicated by the following claims.

What is claimed is:

1. An apparatus for sensing and measuring at least one physiological parameter of a person, the apparatus comprising:
   a housing comprising a front face, a rear face, and an interior region located between the front face and the rear face, at least a portion of the rear face configured for contact with a targeted area;
   a sensor for sensing at least one physiological parameter, the sensor comprising at least one light source for illuminating the targeted area, at least one optical detector for receiving reflected light from the targeted area, and at least one substrate to which the at least one light source and the at least one optical detector are mounted; and
   at least one optical barrier between the at least one light source and the at least one optical detector, the at least one optical barrier comprising a laterally-extending portion and a vertically-extending portion extending from the laterally-extending portion toward the targeted area, both portions positioned on a same side of the substrate as the at least one light source and the at least one optical detector for preventing direct light transmission from the at least one light source to the at least one optical detector.

2. The apparatus of claim 1, wherein each light source and each optical detector are associated with a respective transparent member that facilitates transmission of light and comprises a contact surface for contacting the targeted area.

3. The apparatus of claim 2, wherein one or more transparent members comprises an epoxy or lens.

4. The apparatus of claim 2, wherein each transparent member is at least partially positioned in an associated opening that extends through the housing.

5. The apparatus of claim 4, wherein the contact surface of one or more transparent members is substantially flush with the housing.

6. The apparatus of claim 2, wherein the housing comprises a raised region outwardly projecting from the rear face.

7. The apparatus of claim 6, wherein each transparent member is at least partially positioned in an associated opening that extends through the raised region and the contact surface of one or more transparent members is substantially flush with the raised region.

8. The apparatus of claim 7, wherein at least a portion of the rear surface is curved to substantially correspond with a curvature of the targeted area.

9. A device for monitoring at least one physiological parameter of a person, the device comprising:
   an elongate body comprising a front face, a rear face, and an interior region defined between the front and rear faces, at least a portion of the rear face configured for contacting a targeted tissue region;
   a sensor for detecting at least one physiological parameter of the person comprising at least one light source, at least one optical detector, and at least one substrate to which the at least one light source and the at least one optical detector are mounted; and at least one optical barrier between the at least one light source and the at least one optical detector, the at least one optical barrier comprising a laterally-extending portion and a vertically-extending portion extending from the laterally-extending portion outward to the targeted tissue region, both portions positioned on a same side of the substrate as the at least one light source and the at least one optical detector for preventing light transmission from the at least one light source directly to the at least one optical detector.

10. The device of claim 9, wherein the sensor comprises a contact surface configured for contact with the targeted tissue region.

11. The device of claim 10, further comprising at least one translucent member comprising the contact surface.

12. The device of claim 11, wherein the at least one translucent member is an epoxy or lens.

13. The device of claim 12, wherein the rear face comprises an outwardly protruding raised region, the raised region comprising at least one aperture for at least partially receiving the sensor.

14. The device of claim 13 wherein the raised region comprises an outwardly protruding further raised region, the contact surface being substantially flush with the further raised region.

15. The device of claim 14 wherein the further raised region is substantially concentric with the raised region.

16. A wearable apparatus for monitoring at least one physiological parameter, the apparatus comprising:

a body comprising a rear face, at least a portion of the rear face configured for contact with a targeted area;

an optical sensor comprising at least one light source, at least one optical detector, at least one substrate to which the at least one light source and the at least one optical detector are mounted, and at least one substantially transparent member; and at least one optical barrier comprising a laterally-extending portion and a vertically-extending portion extending between the laterally-extending portion and the targeted area, both portions positioned on a same side of the substrate as the at least one light source and the at least one optical detector for preventing light transmission from the at least one light source directly to the at least one optical detector.

17. The apparatus of claim 16, wherein the rear face comprises a base region and a raised region extending beyond the base region, the optical sensor being positioned at least partially within the raised region.

18. The apparatus of claim 17, wherein the raised region comprises a further raised region extending beyond at least a portion of the raised region, the optical sensor being positioned at least partially within the further raised region.

19. The apparatus of claim 16, wherein the optical sensor comprises a pair of light sources and the optical detector is positioned between, and substantially equidistant from, the pair of light sources.

* * * * *